US010638782B2

(12) United States Patent
Womack et al.

(10) Patent No.: US 10,638,782 B2
(45) Date of Patent: May 5, 2020

(54) PROFLAVOR DELIVERY PARTICLES

(71) Applicant: Firmenich SA, Satigny (CH)

(72) Inventors: Gary B. Womack, Hopewell, NJ (US);
Rutger M. T. Van Sleeuwen,
Somerville, NJ (US)

(73) Assignee: Firmenich SA, Satigny (CH)

( * ) Notice: Subject to any disclaimer, the term of this patent is extended or adjusted under 35 U.S.C. 154(b) by 151 days.

(21) Appl. No.: 15/539,013

(22) PCT Filed: Dec. 21, 2015

(86) PCT No.: PCT/EP2015/080719
§ 371 (c)(1),
(2) Date: Jun. 22, 2017

(87) PCT Pub. No.: WO2016/102426
PCT Pub. Date: Jun. 30, 2016

(65) Prior Publication Data
US 2018/0103667 A1 Apr. 19, 2018

Related U.S. Application Data

(60) Provisional application No. 62/096,839, filed on Dec. 24, 2014.

(51) Int. Cl.
A23L 27/29 (2016.01)
A23L 2/56 (2006.01)
(Continued)

(52) U.S. Cl.
CPC ............. A23L 27/2024 (2016.08); A23L 2/56 (2013.01); A23L 27/29 (2016.08); C07C 69/38 (2013.01);
(Continued)

(58) Field of Classification Search
CPC ........ A23L 27/2024; A23L 27/29; A23L 2/56; A23L 27/72; C07C 69/38; C07C 69/40; C07C 69/44; C07C 69/60; C07D 307/12
See application file for complete search history.

(56) References Cited

U.S. PATENT DOCUMENTS 4,419,280 A * 12/1983 Boden .................. C11B 9/0019
512/26
5,079,023 A 1/1992 DeSimone
(Continued)

FOREIGN PATENT DOCUMENTS

JP 2000159843 A 6/2000
JP 2013182040 A 9/2013
(Continued)

OTHER PUBLICATIONS

Lukic et al "Characterization and Differentiation of Monovarietal Grape Marc Distillates on the Basis of Varietal Aroma Compound Composition", Journal of Agricultural and Food Chemistry, 2010, 58(12), pp. 7351-7360.*
(Continued)

Primary Examiner — Nikki H. Dees
Assistant Examiner — Changqing Li
(74) Attorney, Agent, or Firm — Armstrong Teasdale LLP

(57) ABSTRACT

Provided herein are flavor particles containing encapsulated precursors of acetylaldehyde. Also provided herein are methods of making and using the particles.

14 Claims, 4 Drawing Sheets

(51) Int. Cl.
    *C07D 307/12*     (2006.01)
    *A23L 27/20*     (2016.01)
    *C07C 69/38*     (2006.01)
    *C07C 69/40*     (2006.01)
    *C07C 69/44*     (2006.01)
    *C07C 69/60*     (2006.01)
    *A23L 27/00*     (2016.01)

(52) U.S. Cl.
    CPC .............. *C07C 69/40* (2013.01); *C07C 69/44* (2013.01); *C07C 69/60* (2013.01); *C07D 307/12* (2013.01); *A23L 27/72* (2016.08)

(56) References Cited

U.S. PATENT DOCUMENTS

| | | | |
|---|---|---|---|
| 6,235,956 B1* | 5/2001 | Hugues | C07C 43/303 |
| | | | 585/511 |
| 8,017,060 B2* | 9/2011 | Benczedi | A23L 27/80 |
| | | | 264/411 |
| 2005/0026998 A1 | 2/2005 | Womack et al. | |
| 2010/0193023 A1 | 8/2010 | Karpinski et al. | |
| 2012/0270979 A1 | 10/2012 | Hsu et al. | |
| 2015/0232691 A1* | 8/2015 | Webster | C08F 222/02 |
| | | | 523/400 |
| 2017/0044089 A1* | 2/2017 | Messana | C08F 2/44 |
| 2017/0339993 A1* | 11/2017 | Womack | A23L 27/2024 |

FOREIGN PATENT DOCUMENTS

| | | |
|---|---|---|
| WO | WO2003056938 A1 | 7/2003 |
| WO | WO2014128071 A1 | 8/2014 |

OTHER PUBLICATIONS

Sorrel, Chapter 19.1d, Organic Chemistry, 2nd Edition, University Science Books, 2006.*

International Search Report and Written Opinion, application PCT/EP2015/080719 dated Mar. 31, 2016.

Williams et al, "Hydroxylated Linalool Derivatives as Precursors of Volatile Monoterpenes of Muscat Grapes," J. Agric. Food Chem., vol. 28, No. 4, 1980, pp. 766-771.

Furia et al, "Fenaroli's Handbook of Flavor Ingredients," XP-002102351, 1975, pp. 543, 656.

* cited by examiner

PROFLAVOR DELIVERY PARTICLES

RELATED APPLICATIONS

This application is a national stage application under 35 U.S.C. § 371 filing of International Patent Application PCT/EP2015/080719, filed Dec. 21, 2015, which claims the benefit of U.S. Provisional Application 62/096,839, filed Dec. 24, 2014.

FIELD

Provided herein are precursors (proflavors) to acetaldehyde and their use for delivering acetaldehyde to food and beverages to typically provide an increase/enhancement of flavor.

BACKGROUND

Acetaldehyde is an important, yet difficult to encapsulate flavor ingredient. It is used in a large variety of flavors but is particularly appreciated in fruit flavors where it imparts important aspects of freshness and juiciness to the flavors. The volatility of acetaldehyde also provides lift to the aroma greatly contributing to the olfactive impact of the flavor. Thus the use of acetaldehyde is indispensable for creating flavors where these effects are desired such as in beverages. However, with a boiling point of 20-21° C., it is a difficult material to use due to evaporation during handling which in turn can create unsafe situations due to overexposure to personnel and the risk of fire. Once incorporated into a liquid flavor, loss of acetaldehyde due to evaporation is still a concern, which also can make handling such flavors difficult. In addition to being highly volatile, acetaldehyde is a very reactive chemical. It can react with alcohols in flavor formulations to form acetals; it can engage in aldol condensation reactions; it is susceptible to oxidation; and it can trimerize to form paraldehyde. In addition to losing acetaldehyde by these chemical reactions, the products formed can change the character of the flavor and in the worst case contribute unwanted off-flavors.

Extrusion processes have been used to encapsulate flavors. It is desirable to obtain compositions of precursors of acetaldehyde that remain stable until the acetaldehyde is released into a food or beverage.

SUMMARY

Provided herein is a glassy particle or bead composition comprising:
a) a compound selected from the group consisting of a compound of Formula I

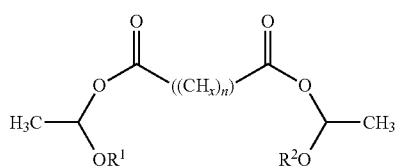

wherein R1 and R2 are independently selected from a branched or straight $C_1$-$C_6$ and a $C_1$-$C_6$ alkenyl, n is 1, 2, 3, 4, 5 or 6 and x is independently 0, 1 or 2 provided that when n is 1, x is 2, and 5-(2-(1-ethoxyethoxy)propan-2-yl)-2-methyl-2-vinyltetrahydrofuran;

b) a carrier comprising a carbohydrate; wherein the carrier is provided in an amount, by weight, up to about 90% of the total weight of the particle; and
c) water.

Further provided herein is a method of releasing acetaldehyde into an aqueous solution comprising delivering a glassy particle or bead as described above comprising delivering the composition as defined above to the aqueous solution.

In a further embodiment provided herein is the use of a glassy particle or bead as defined above to confer, enhance, improve or modify the flavor or aroma of a flavored article.

Further provided herein is a method of making a glassy composition comprising:
i) blending in an extruder
   a) a compound selected from the group consisting of a compound of formula I

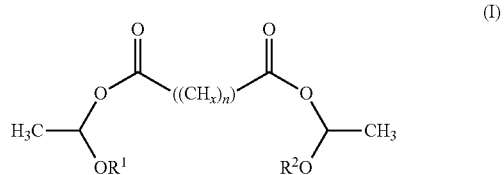

wherein R1 and R2 are independently selected from a branched or straight $C_1$-$C_6$ alkyl and a $C_1$-$C_6$ alkenyl, n is 1, 2, 3, 4, 5 or 6 and x is independently 0, 1 or 2; provided that when n is 1, x is 2; and 5-(2-(1-ethoxyethoxy)propan-2-yl)-2-methyl-2-vinyltetrahydrofuran;
   b) a carrier comprised of a carbohydrate;
   c) optionally a lubricant;
   d) water, and optionally
   e) an emulsifier;
ii) heating the blend to a temperature sufficient to form a molten mass;
iii) extruding the molten mass;
iv) cutting the molten mass into granules; and
v) allowing the granules to cool to form glassy particles.

DESCRIPTION OF THE INVENTION

Figure 1:
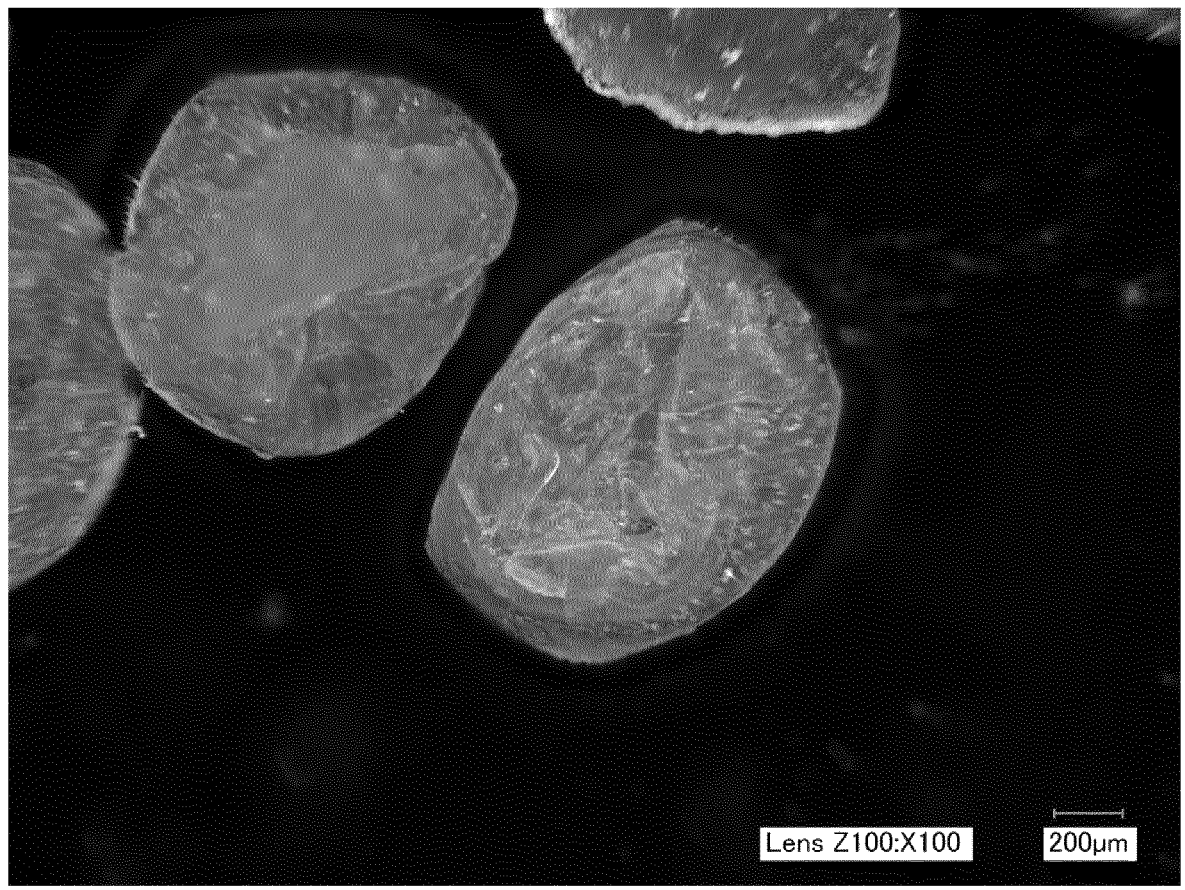
FIG. 1 shows a Reflected Light Microscopy stacked image of Control particle made by Twin Screw Extrusion.

For the Summary, Description and Claims, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of".

5-(2-(1-ethoxyethoxy)propan-2-yl)-2-methyl-2-vinyltetrahydrofuran is represented by the formula

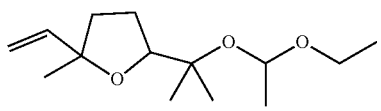 [SMILES: C=CC1(C)CCC(C(C)(C)OC(C)OCC)O1]

The carrier provided herein is a carrier comprising a carbohydrate and optionally a polymeric emulsifier. In a particular embodiment, the carrier is provided in an amount that ranges, by weight, of about 40% to about 99%, particularly from about 70% to about 90%, more particularly from about 80% to about 90% of the total weight of the particle or bead. In another particular embodiment the carrier is provided in an amount of about 85% of the total weight of the particle or bead.

In a particular embodiment, provided herein is a carrier comprising a carbohydrate or carbohydrate derivative which can be readily processed through extrusion techniques to form a dry extruded solid. Particular examples of suitable materials include those selected from the group consisting of sucrose, glucose, lactose, maltose, fructose, ribose, dextrose, isomalt, sorbitol, mannitol, xylitol, lactitol, maltitol, pentatol, arabinose, pentose, xylose, galactose, trehalose, hydrogenated corn syrup, maltodextrin, agar, carrageenan, gums, polydextrose, starch and derivatives and mixtures thereof. Other suitable carrier ingredients are cited in reference texts such as H. Scherz, Hydrokolloide: Stabilisatoren, Dickungs- und Geliermittel in Lebensmittel, Band 2 der Schriftenreihe Lebensmittelchemie, Lebensmittelqualitat, Behr's Verlag GmbH & Co, Hamburg, 1996. In a particular embodiment provided herein comprises a maltodextrin having a dextrose equivalent not above twenty (≤20 DE).

Particularly, the carbohydrate may comprise a non-emulsifying water soluble material such as, but not limited to, maltodextrins. In a particular embodiment, the carbohydrate is a maltodextrin with a dextrose equivalent (DE) of about 1 to about 20. In a particular embodiment, the maltodextrin is selected from a maltodextrin with a DE of about 10 up to about 18 DE. In another embodiment, the carbohydrate comprises corn syrup with a DE from 21 up to 49. Any carbohydrate can be used that is made by the hydrolysis of starches from different origins such as, but not limited to, maize, wheat, potato or rice. In another embodiment, the carbohydrate is a hydrogenated starch hydrolysate (e.g., HSPolyols), fructose oligosacharides (e.g., but not limited to Inulin from Orafit), soluble fibers such as for example but not limited to Nutriose (Roquette) and pregelatinized starch.

In a further embodiment, the carrier comprises a emulsifier in an amount of from about 0% up to about 100%, by weight, of the total weight of the carrier. In yet another embodiment, the emulsifier is provided in an amount of about 5% up to about 100%, by weight of the total weight of the carrier. In one embodiment, the emulsifier is a polymeric emulsifier. In another aspect, the carrier comprises a polymeric emulsifier which comprises a material such as Capsul® (Ingredion). In another embodiment, the emulsifier is an alkenyl succinated starch, more particularly an octenyl succinated starch (OSS). Some particular example, but not limited to, are N-Lok®, Purity Gum® (Ingredion) and EmCap® (Cargill). In another embodiment, the emulsifier is Gum Arabic.

In a particular embodiment, the emulsifier may be provided in an amount, by weight, from about 5% to about 60%, particularly from about 5% to about 40%, even more particularly from about 10% to about 40%, and more particularly at about 10% of the total weight of the carrier.

In another embodiment, a lubricant is provided herein. While not wishing to be bound to any theory it is believed that the lubricant reduces shear and expansion of the molten mass at the exit die. In some embodiments, the lubricant may comprise a medium chain triglyceride (MCT). In another embodiment, the lubricant comprises a micellar surfactant like lecithin or a fatty acid ester (e.g., citric, tartaric, acetic), DATEM, CITREM or mixtures of the above. In a particular embodiment, the lubricant may be provided in an amount, by weight, up to about 5%, particularly about 0.2 up to about 5%, more particularly from about 0.8% up to about 2% and even more particularly about 1% of the total weight of the particle.

In a further embodiment a buffer is provided in the extrusion process to stabilize the compounds provided herein (e.g., the "proflavors") in order to prevent or minimize the acetaldehyde from being released during the processing of the particles.

In a particular embodiment, a buffer is added or injected into a carrier mixture prior to or during the extrusion process. This buffer is preferably a food grade buffer for example, but not limited to a GRAS or food additive raw material. Some non-limiting examples of suitable buffers based on citric acid, acetic acid and phosphoric acid, sodium acetate, disodium acetate, trisodium acetate, monobasic potassium phosphate, dibasic potassium phosphate, monobasic sodium phosphate, dibasic sodium phosphate, tribasic sodium phosphate.

In one embodiment, the buffer maintains the pH of the mixture in such a way to minimize the release of acetaldehyde from the precursor compounds during processing.

In one embodiment, the buffer is included in the composition in an amount effective to maintain the pH of the extrusion mixture and the particles from 4 to about 9, particularly from 5 to about 8. In a particular embodiment the pH is from about 6 to about 7, more particularly at about 7.

In a particular embodiment a carbohydrate, and at least one emulsifier are mixed and a compound provided herein is dispersed into the mix. In one embodiment, water is added to the mix until a free flowing powder is formed. Ideally the water is added without forming lumps. The components of the mixture described above can be premixed for example in a bowl or even stepwise into an extruder. The components may be mixed prior to being added to the extruder or alternatively, added stepwise, or injected or as a mixture of one or more of the components that make up the particle.

In some embodiments, the water acts as a plasticizer. The amount of water may be adjusted to obtain a glass transition temperature (Tg) between 30 and 100° C., more particularly at about 40-50° C. In another embodiment, the water may be added to the process for making the glass transition in a desired range. In one embodiment the water is provided in an amount, by weight of about 0.1 to 10%, more particularly from about 0.1% to about 6%.

In one embodiment, a buffer is added to the process to control the pH of the mixture.

The blended powder may then be extruded. In a particular embodiment, the powder may be extruded at a throughput of 500 g/h through a 0.7 mm die hole using for example, but not limited to a Thermo Prism 16 mm twin-screw lab extruder or a Clextral BC-21 equipped with a cutter knife in order to granulate the melt at the die exit. In another embodiment, the melt may be extruded for example as strands and allowed to cool and then cut or crushed. In a particular embodiment, the screws are configured so that they have two mixing zones. In a further embodiment the temperature set point profile may be 80° C.-100-105-108° C. from the inlet of the extruder to the die plate. The temperature of the melt may range from about 20° C. at the inlet to about 80° C. to around 120° C. near the die. In a particular embodiment, the temperature of the mix is about 108° C.

In one embodiment, the extruder comprises 2 to 8 heating and cooling zones with temperatures ranging from 20 to about 120° C.

The extruder may also comprise at least two mixing zones.

In a further embodiment, the temperature ranges at the die exit ranges from about 90 to about 130° C. and particularly at about 100° C. In a particular embodiment, the pressure is maintained below 100 bar. Particularly, the temperature at the die exit may be around 50° C. higher than the expected Tg.

The softening or glass transition temperature is preferably kept above 40° C. to guarantee the free flowing nature of the produced powder at ambient temperature. An appropriate amount of water may be added to the mixture to guarantee that the carrier's glass transition temperature is well above room temperature and preferably above 40° C. The glass transition temperature of the particles provided herein depends on the amount of water added to the initial mixture. The Tg decreases when the proportion of water increases. Ideally, the proportion of water added to the mixture will be low, i.e., such that the glass transition temperature of the resulting mixture is substantially equal to the glass transition temperature desired for the final flavor or fragrance delivery system, i.e., the extruded product. In one embodiment a glass transition temperature Tg is provided significantly above the temperature at which the particle will be stored and subsequently used. Ideally, the temperature should be at least above room temperature and preferably above 40° C. The proportions in which water is employed may therefore vary in a wide range of values which the skilled person is capable of adapting and choosing as a function of the composition used in the matrix and the required Tg of the final product. For instance, for a carbohydrate glass having a DE (dextrose equivalent) of 18, proportions from 5 to 10% of water in the mixture can be used.

In some embodiments, the size (diameter) of the particle or bead provided herein ranges in size from about 0.1 mm up to about 5 mm, particularly from about 0.5 mm up to about 2 mm, more particularly from about 0.5 mm up to about 1.4 mm, more particularly from 0.5 mm up to 1 mm and even more particularly at about 0.6, 0.7 or 1.4 mm.

In one embodiment, the resulting particles show a dense non-expanded morphology.

The compounds provided herein are precursors of acetaldehyde in that they act as a "proflavor" and release acetaldehyde by hydrolysis when exposed to water.

In some embodiments the particle comprises the encapsulated compound in an amount greater than or equal to 0.01% to about 15%, by weight, of the total weight of the particle. In another particular embodiment, the compounds provided herein are provided in an amount of about 1% to 15%, particularly from 1% to 5%, and more particularly from about 1% to 2%, of the total weight of the particle.

The compounds provided herein comprise a compound of Formula I wherein $R^1$ and $R^2$ are independently a straight or branched $C_1$-$C_4$.

In one embodiment, provided herein is a compound of Formula I wherein $R^1$ and $R^2$ are independently selected from the group consisting of methyl, ethyl, propyl, and butyl.

In another embodiment, provided herein is a compound of Formula I wherein n is 1 and x is 2.

In another embodiment, provided herein is a compound of Formula I wherein n is 2 and x is independently 0, 1 or 2.

In another embodiment, provided herein is a compound of Formula I wherein n is 3, 4, 5 or 6 and x is independently 0, 1 or 2.

In another embodiment provided herein is a compound of Formula I selected from the group consisting of: bis(1-ethoxyethyl) succinate; bis(1-ethoxyethyl) adipate; bis(1-ethoxyethyl) fumarate; bis(1-propoxyethyl) succinate; bis(1-propoxyethyl) adipate; bis(1-propoxyethyl) fumarate; bis(1-butoxyethyl) succinate; bis(1-butoxyethyl) adipate, and bis(1-butoxyethyl) fumarate.

In a particular embodiment provided herein is a compound of Formula I selected from the group consisting of bis(1-ethoxyethyl) succinate; bis(1-ethoxyethyl) adipate; bis(1-ethoxyethyl) fumarate; bis(I-propoxyethyl) succinate; bis(1-propoxyethyl) adipate; bis(1-propoxyethyl) fumarate; bis(1-butoxyethyl) succinate; and bis(1-butoxyethyl) adipate.

In another embodiment, provided herein is a compound of Formula I comprising bis(1-ethoxyethyl) succinate.

In another embodiment, provided herein is a compound of Formula I comprising bis(1-propoxyethyl) succinate.

In another embodiment, provided herein is a compound of Formula I comprising bis(1-butoxyethyl) succinate.

In another embodiment, provided herein is a compound of Formula I comprising bis(1-ethoxyethyl) adipate.

In another embodiment, provided herein is a compound of Formula I comprising bis(1-propoxyethyl) adipate.

In another embodiment, provided herein is a compound of Formula I comprising bis(1-butoxyethyl) adipate.

In another embodiment, provided herein is a compound of Formula I comprising bis(1-ethoxyethyl) fumarate.

In another embodiment, provided herein is a compound of Formula I comprising bis(1-propoxyethyl) fumarate.

In another embodiment, provided herein is a compound of Formula I comprising bis(1-butoxyethyl) fumarate.

In another embodiment, provided herein is S-(2-(1-ethoxyethoxy)propan-2-yl)-2-methyl-2-vinyltetrahydrofuran.

The compounds provided herein and the methods of making them can be found in U.S. Provisional Application Nos. 62/096,830 and 62/096,835 file on even date herewith. The contents of both applications are incorporated by reference in their entirety herein.

The compositions provided herein may also additionally comprise a flavor. In a particular embodiment the flavors have a Log P of >2 with a Mw<600 Daltons.

The particles provided herein may further comprise an additional flavor. By use of the word "Flavor" it is meant here a flavoring ingredient or a mixture of flavoring ingredients, solvents or adjuvants of current use for the preparation of a flavoring formulation, i.e. a particular mixture of ingredients which is intended to be added to an edible composition or chewable product to impart, improve or modify its organoleptic properties, in particular its flavor and/or taste. Flavoring ingredients are well known to a person skilled in the art and their nature does not warrant a detailed description here, which in any case would not be exhaustive, the skilled flavorist being able to select them on the basis of his general knowledge and according to the intended use or application and the organoleptic effect it is desired to achieve. Many of these flavoring ingredients are listed in reference texts such as in the book by S. Arctander, Perfume and Flavor Chemicals, 1969, Montclair, N.J., USA, or its more recent versions, or in other works of similar nature such as Fenaroli's Handbook of Flavor Ingredients, 1975, CRC Press or Synthetic Food Adjuncts, 1947, by M. B. Jacobs, van Nostrand Co., Inc. Solvents and adjuvants of current use for the preparation of a flavoring formulation are also well known in the art.

The phrase flavor includes not only flavors that impart or modify the smell of foods but include taste imparting or modifying ingredients. The latter do not necessarily have a taste or smell themselves but are capable of modifying the taste that other ingredients provide, for instance, salt enhancing ingredients, sweetness enhancing ingredients, umami enhancing ingredients, bitterness blocking ingredients and so on.

In a further embodiment, suitable sweetening components may be included in the particles described herein. In a particular embodiment, a sweetening component is selected from the group consisting of sugar (e.g., but not limited to sucrose), a stevia component (such as but not limited to stevioside or rebaudioside A), sodium cyclamate, aspartame, sucralose, sodium saccharine, and Acesulfame K or mixtures thereof.

In one embodiment, the compositions and compounds provided herein provide "fresh", "juicy" and "fruity" flavor and/or aroma to a food article.

A particle provided herein containing a compound selected from the group consisting of a compound of formula (I) and 5-(2-(1-ethoxyethoxy)propan-2-yl)-2-methyl-2-vinyltetrahydrofuran can be incorporated into a flavored articles to positively impart, or modify, the freshness or fruity flavor or aroma of said articles. Thus, in yet another aspect, the present invention provides a flavored article comprising:
i) a particle comprising a compound selected from the group consisting of formula (I) and 5-(2-(1-ethoxyethoxy)propan-2-yl)-2-methylyl-2-vinyltetrahydrofuran, as defined and
ii) a foodstuff base.

For the sake of clarity, it has to be mentioned that, by "foodstuff" we mean here an edible product, e.g. a food or a beverage. Therefore, a flavored article according to the invention comprises one or more compounds according to formula (I) or 5-(2-(1-ethoxyethoxy)propan-2-yl)-2-methyl-2-vinyhetrahydrofuran, as well as optional benefit agents, corresponding to a flavor or aroma and flavor or aroma profile of the desired edible product. The compositions and methods provided herein have use in food or beverage products. When the food product is a particulate or powdery food, the dry particles may easily be added thereto by dry-mixing. Typical food products are selected from the group consisting of an instant soup or sauce, a breakfast cereal, a powdered milk, a baby food, a powdered drink, a powdered chocolate drink, a spread, a powdered cereal drink, a chewing gum, an effervescent tablet, a cereal bar, and a chocolate bar. The powdered foods or drinks may be intended to be consumed after reconstitution of the product with water, milk and/or a juice, or another aqueous liquid.

Suitable foodstuff bases, e.g. foods or beverages, include dairy and confectionary products where a fresh or fruity tonality is desired.

In another embodiment provided herein is a fluid dairy product including without limitation, non-frozen, partially frozen and frozen fluid dairy products such as, for example, milks, ice creams, sorbets and yogurts.

Beverage products include, without limitation, carbonated soft drinks, including cola, lemon-lime, root beer, heavy citrus ("dew type"), fruit flavored and cream sodas; powdered soft drinks, as well as liquid concentrates such as fountain syrups and cordials; coffee and coffee-based drinks, coffee substitutes and cereal-based beverages; teas, including dry mix products as well as ready-to-drink teas (herbal and tealeaf based); fruit and vegetable juices and juice flavored beverages as well as juice drinks, nectars, concentrates, punches and "ades"; sweetened and flavored waters, both carbonated and still; sport/energy/health drinks; alcoholic beverages plus alcohol-free and other low-alcohol products including beer and malt beverages, cider, and wines (still, sparkling, fortified wines and wine coolers); other beverages processed with heating (infusions, pasteurization, ultra high temperature, ohmic heating or commercial aseptic sterilization) and hot-filled packaging; and cold-filled products made through filtration or other preservation techniques. The nature and type of the constituents of the foodstuffs or beverages do not warrant a more detailed description here, the skilled person being able to select them on the basis of his general knowledge and according to the nature of said product.

In one embodiment, a compound provided herein is provided in the glass particle or bead in an amount that ranges by weight, of about 0.01% to 15%, particularly from about 1% to about 15%, more particularly from about 1% to about 5%, and more particularly from about 1% to about 2% of the total weight of the particle. In one embodiment, the concentration of the compounds provided herein (delivered as a glassy particle) in a flavored article are in the range, by weight, of about 3 ppm to about 60 ppm, particularly from about 3 ppm to about 30 ppm, more particularly from about 12 ppm to about 30 ppm, even more particularly from about 12 ppm to 15 ppm based on the total weight of the flavored article.

In another embodiment, the compounds provided herein are provided in an amount in a flavored article such that the particles release a compound provided herein that further release acetaldehyde in the flavored article when exposed to an aqueous solution wherein the acetaldehyde is released in an amount that ranges from about 1 ppm to about 20 ppm, more particularly from about 1 ppm to about 10 ppm, more particularly from 4 ppm to about 10 ppm, even more particularly from about 4 ppm to about 6 ppm of the total weight of the article.

The following Examples are illustrative only and are not meant to limit the scope of the claims, the Summary or any invention presented herein.

EXAMPLES

Twin Screw Extrusion of Acetaldehyde Precursors in Carbohydrate Matrix.

Three separate formulations and a control sample were manufactured by twin screw extrusion. The approximate formulations in weight % are summarized in Table 1 and a more detailed explanation is given below for each of the three examples.

TABLE 1

Summary of Compositions of various Twin Screw Extruded samples

| Compound | Example 1 Formulation in Weight % | Example 2 Formulation in Weight % | Example 3 Formulation in Weight % | Control Formulation in Weight % |
|---|---|---|---|---|
| bis(1-ethoxyethyl)adipate | 1.43% | — | — | — |
| bis(1-ethoxyethyl)-succinate | — | 1.40% | — | — |
| 5-(2-(1-ethoxyethoxy)propan-2-yl)-2-methyl-2-vinyltetrahydrofuran | — | — | 1.40% | — |
| ORANGE OIL CALIFORNIA ARR 968585 (Sunkist Growers) | 4.30% | 4.25% | 4.21% | 4.21% |
| Maltodextrin (Glucidex IT 19, Roquette Corporation, Lestrem, France) | 86.69% | 86.54% | 86.02% | 87.51% |
| Deionized water | 5.48% | 5.49% | 5.46% | 5.46% |
| Color Red Cabbage Powder (Sensient) | 0.05% | 0.05% | 0.05% | 0.05% |
| Monosodium phosphate anh. (Haifa chemicals) | 0.06% | 0.06% | 0.06% | 0.06% |
| Disodium phosphate (Haifa chemicals) | 0.1% | 0.09% | 0.09% | 0.09% |
| Lecithin (Cargill) | 0.95% | 1.06% | 1.35% | 1.31% |
| Neobee M5 (Oleon) | 0.95% | 1.06% | 1.35% | 1.31% |

Control Sample

The appearance of the Control Sample (FIG. 1) shows a typical particle made by twin screw extrusion that has an unexpanded appearance since it contains only orange oil as the predominant volatile ingredient and 0.00% acetaldehyde; as determined by HPLC with UV/VIS detection after DNPH (2,4-dinitrophenylhydrazine) derivatization. During extrusion of this sample a small amount of puffing/expansion was noted that was minimal.

Example 1

A BC-21 co-rotating twin screw extruder (Clextral, Firminy France, L/D=32) was used to encapsulate the flavor precursor into a solid particulate form. The powder feed consisted of Maltodextrin 18DE and Red Cabbage powder (0.05 wt %). The cabbage powder served merely as a visual pH indicator. The powder was fed into the extruder by means of a loss-in-weight powder feeder with a set point of 9.2 kg/hr. An emulsifier (soy lecithin/Neobee M5) was injected at a rate of 201 g/hr. Temperature set points on the extruder barrels ranged from 20-100° C.

Bis(1-ethoxylethyl) adipate was mixed with Orange Oil (25/75 wt %). This mixture was injected at a flow rate of 608 grams per hour on a total flow rate of 10.6 kg/h. A buffer was prepared by mixing 43.5 g of monosodium phosphate anh. and 69.5 g disodium phosphate and dissolved in 4000.8 g deionized water. The pH=7 of the buffer was verified using a pH-indicator strip. This buffered water was injected at 598 grams per hour. The flavor precursor injection location was positioned about 80% of the axial distance between inlet and die. Therefore, the time/distance the flavor precursor resides inside the extruder was relatively short.

Figure 2:
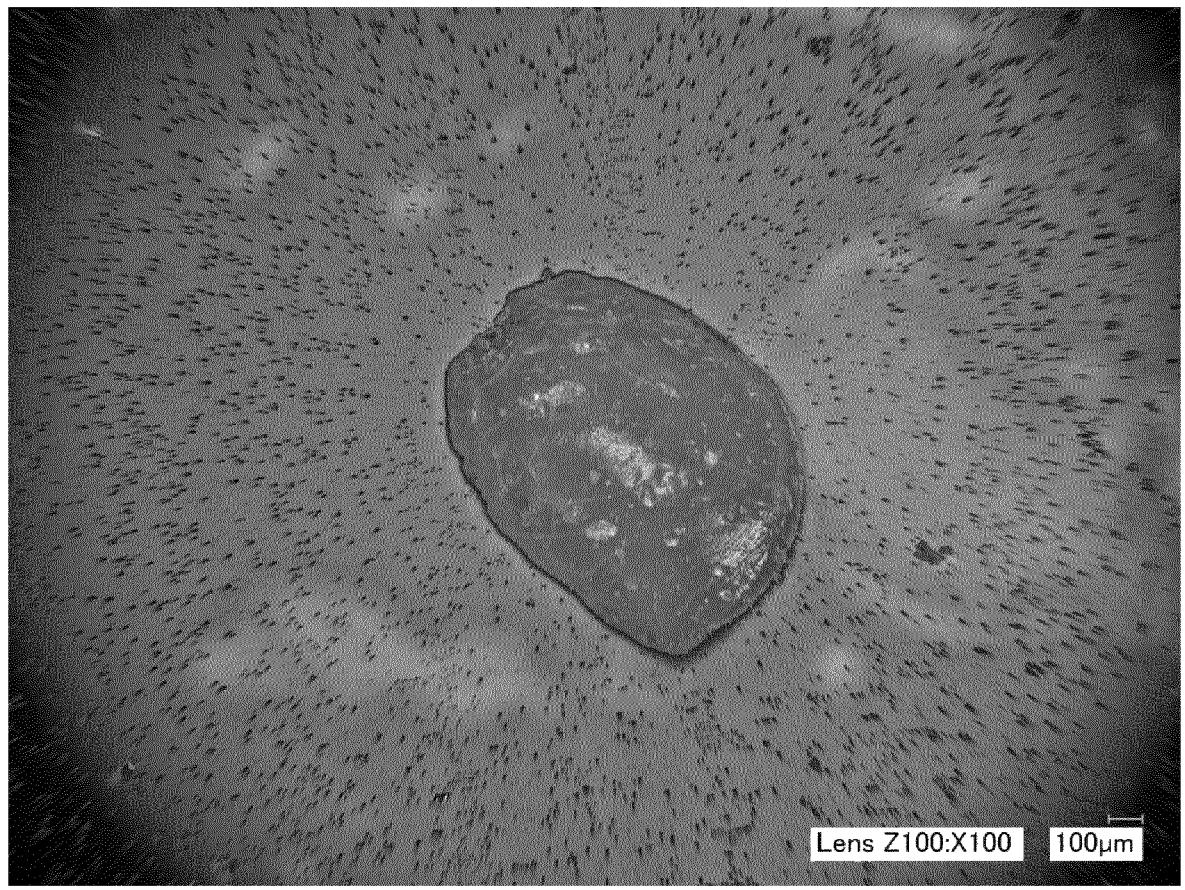
FIG. 2 shows a Reflected Light Microscopy stacked image of encapsulated bis(1-ethoxyethyl) adipate Proflavor particle made by Twin Screw Extrusion.

The carbohydrate melt was extruded through a die plate with 1-mm diameter holes. After establishing steady-state extrusion condition, particles were cut by means of rotating cutting blades/knives and particles were sieved between 710 and 1,400 μm. Upon injection of the flavor precursor, a very small amount of bubbling/puffing was observed. This suggests that there was a certain amount of conversion of the proflavor into acetaldehyde during processing, but this expansion was minimal. The resulting particles show a dense non-expanded product as can be seen in FIG. 2.

An important physical characteristic of these solid particles is the glass transition temperature. It is well known—that glassy carbohydrate particles with a glass transition temperature exceeding the ambient temperature generally are free-flowing and protect the active better than particles that are rubbery (glass transition temperature below ambient). The particles had a glass transition temperature of 43.0° C. and a moisture content of 8.8% (wet basis).

To analyze the retention of proflavor and acetaldehyde, the proflavor in the particles was converted by an acid and the total acetaldehyde content was analyzed by HPLC with UV/VIS detection after DNPH (2,4-dinitrophenylhydrazine) derivatization. The acetaldehyde content was found to be 0.42% on total wet basis. Bis(1-ethoxyethyl) adipate has a maximum theoretical yield of 30.3% by mass; this means that 1 gram of proflavor can release 0.303 g acetaldehyde if completely converted. Therefore, the actual acetaldehyde retention (proflavor+acetaldehyde) was high; 97%. This means that essentially all acetaldehyde was preserved either as proflavor or as acetaldehyde. Samples were tasted in a tasting solution (7% sugar+0.07% citric acid in spring water and 0.0267% encapsulated proflavor) and compared against the control. Various panelists rated the solution containing the encapsulated proflavor from sample 1 as "juicy" and having a fuller, preferred profile compared to the control. This observation is in line with the good overall acetaldehyde potential as analyzed by HPLC.

Example 2

A BC-21 co-rotating twin screw extruder (Clextral, Firminy France, L/D=32) was used to encapsulate the flavor precursor into a solid particulate form. The powder feed consisted of Maltodextrin 18DE and Red Cabbage powder (0.05 wt %). The cabbage powder served merely as a visual pH indicator. The powder was fed into the extruder by means of a loss-in-weight powder feeder with a set point of 9.2 kg/hr. An emulsifier (soy lecithin/medium chain triglyceride mixture) was injected at a rate of 225 g/hr. Temperature set points on the extruder barrels ranged from 20-100° C.

Bis(1-ethoxylethyl) succinate was mixed with Orange Oil (25/75 wt %). This mixture was injected at a flow rate of 600 grams per hour on a total flow rate of 10.6 kg/h.

A buffer was prepared by mixing 45.8 g of monosodium phosphate anh. and 72.9 g disodium phosphate and dissolved in 4,220.8 g deionized water. The pH=7 of the buffer was verified using a pH-indicator strip. This buffered water was injected at 600 grams per hour. The flavor precursor injection location was positioned about 80% of the axial distance between inlet and die. Therefore, the time/distance the flavor precursor resides inside the extruder was relatively short.

Figure 3:
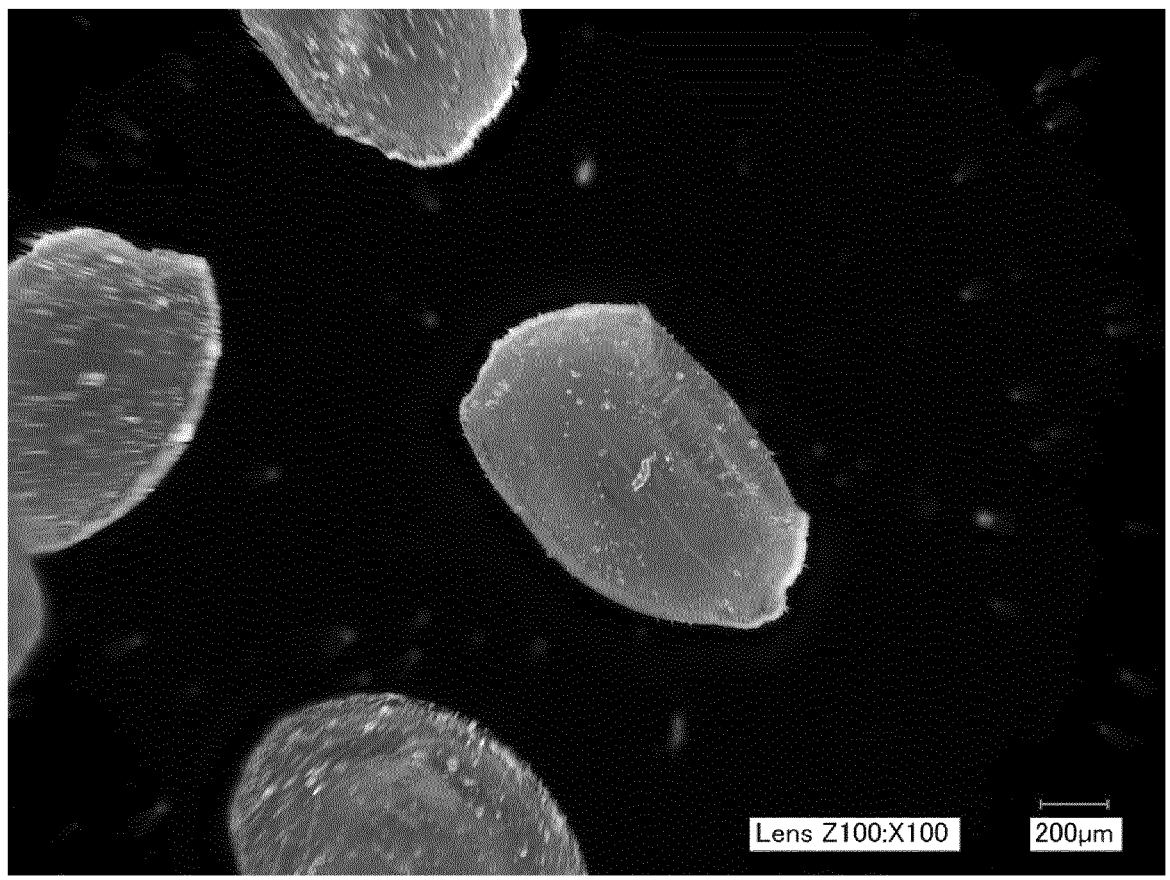
FIG. 3 shows a Reflected Light Microscopy stacked image of encapsulated bis(1-ethoxyethyl) succinate Proflavor particle made by Twin Screw Extrusion.

The carbohydrate melt was extruded through a die plate with 1 mm diameter holes. After establishing steady-state extrusion condition, particles were cut by means of rotating cutting blades/knives and particles were sieved between 710 and 1,400 μm. Upon injection of the flavor precursor, a very small amount of bubbling/puffing was observed. This suggests that there was a certain amount of conversion of the proflavor into acetaldehyde during processing, but this expansion was minimal. The resulting particles show a dense non-expanded product as can be seen in FIG. 3.

The particles had a glass transition temperature of 42.5° C. and a moisture content of 8.1% (wet basis).

To analyze the retention of proflavor and acetaldehyde, the proflavor in the particles was converted by an acid and the total acetaldehyde content was analyzed by HPLC with UV/VIS detection after DNPH (2,4-dinitrophenylhydrazine) derivatization. The acetaldehyde content was found to be 0.48% on total wet basis. Bis(1-ethoxyethyl) succinate has a maximum theoretical yield of 33.5% by mass; this means that 1 gram of proflavor can release 0.335 g acetaldehyde if completely converted. Therefore, the actual acetaldehyde retention (proflavor+acetaldehyde) was high; 103%. This means that essentially all acetaldehyde was preserved either as proflavor or as acetaldehyde.

Samples were tasted in a tasting solution (7% sugar+ 0.07% citric acid in spring water and 0.0267% encapsulated proflavor) and compared against a control. Various panelists rated the solution containing the encapsulated proflavor as "fresh", "juicy" and "fruity". The sample was preferred over the control.

Example 3

A BC-21 co-rotating twin screw extruder (Clextral, Firminy France, L/D=32) was used to encapsulate the flavor precursor into a solid particulate form. The powder feed consisted of Maltodextrin 18DE and Red Cabbage powder (0.05 wt %). The cabbage powder served merely as a visual pH indicator. The powder was fed into the extruder by means of a loss-in-weight powder feeder with a set point of 9.2 kg/hr. An emulsifier (soy lecithin/medium chain triglyceride mixture) was injected at a rate of 289 g/hr. Temperature set points on the extruder barrels ranged from 20-100° C. 5-(2-(1-ethoxyethoxy)propan-2-yl)-2-methyl-2-vinyltetrahydrofuran was mixed with Orange Oil (25/75 wt %). This mixture was injected at a flow rate of 600 grams per hour on a total flow rate of 10.7 kg/h.

A buffer was prepared by mixing 45.8 g of monosodium phosphate anh. and 72.9 g disodium phosphate and dissolved in 4,220.8 g deionized water. The pH=7 of the buffer was verified using indicator strips. This buffered water was injected at 600 grams per hour.

The flavor precursor injection location was positioned about 80% of the axial distance between inlet and die. Therefore, the time/distance the flavor precursor resides inside the extruder was relatively short.

Figure 4:
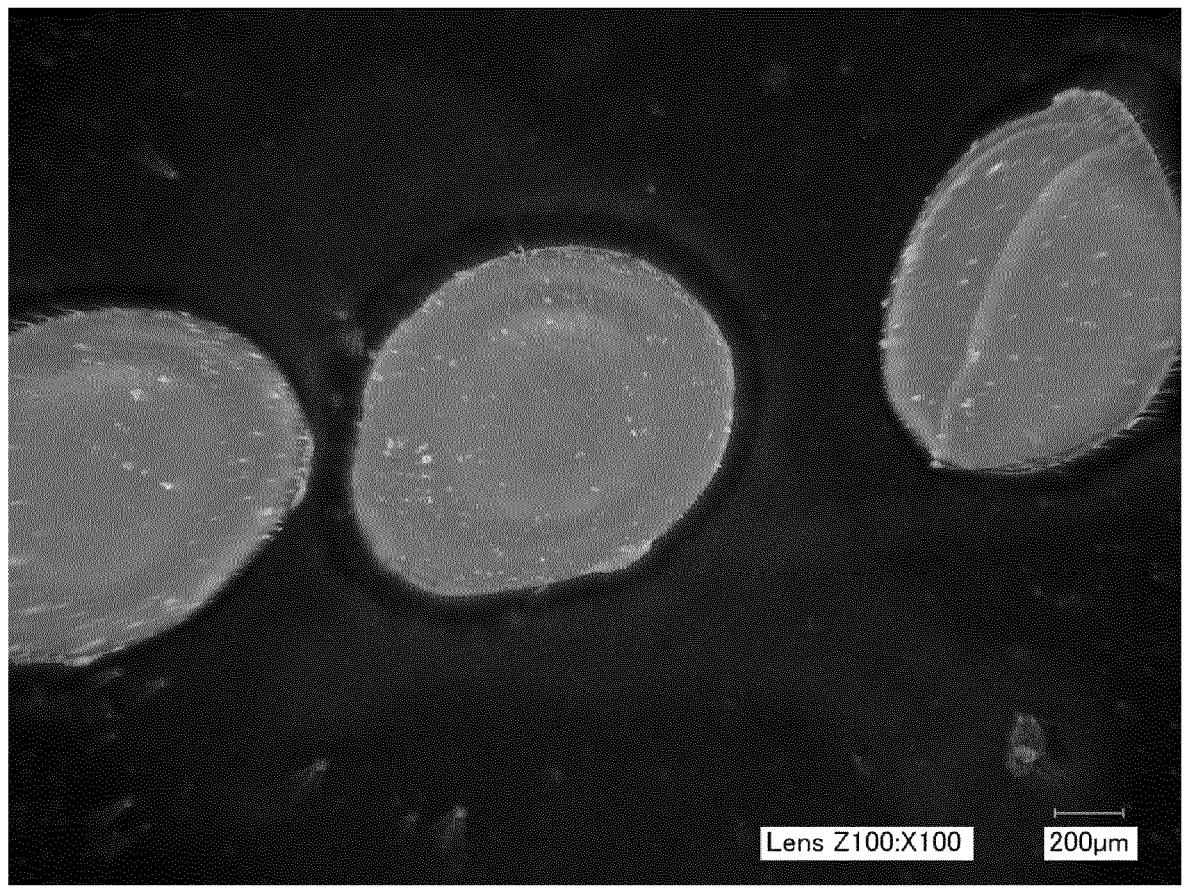
FIG. 4 shows a Reflected Light Microscopy stacked image of encapsulated 5-(2-(1-ethoxyethoxy)propan-2-yl)-2-methyl-2-vinyltetrahydrofuran particle made by Twin Screw Extrusion.

The carbohydrate melt was extruded through a die plate with mm diameter holes. After establishing steady-state extrusion condition, particles were cut by means of rotating cutting blades/knives and particles were sieved between 710 and 1,400 μm. Upon injection of the flavor precursor, a very small amount of bubbling/puffing was observed. This suggests that there was a certain amount of conversion of the proflavor into acetaldehyde during processing, but this expansion was minimal. The resulting particles show a dense non-expanded product as can be seen in FIG. 4.

The particles had a glass transition temperature of 47.7° C. and a moisture content of 8.1% (wet basis). To analyze the retention of proflavor and acetaldehyde, the proflavor in the particles was converted by an acid and the total acetaldehyde content was analyzed by HPLC with UV/VIS detection after DNPH (2,4-dinitrophenyhydrazine) derivatization. The acetaldehyde content was found to be 0.28% on total wet basis. 5-(2-(1-ethoxyethoxy)propan-2-yl)-2-methyl-2-vinyltetrahydrofuran has a maximum theoretical yield of 18.1% by mass; this means that 1 gram of proflavor can release 0.181 g acetaldehyde if completely converted. Therefore, the actual acetaldehyde retention (proflavor+ acetaldehyde) was high; 110%. Values over 100% can be explained due to analytical error and variations in flow rates of ingredients, leading to deviation from the theoretical formulations listed in Table 1. This high retention means that essentially all acetaldehyde was preserved either as proflavor or as acetaldehyde.

Samples were tasted in a tasting solution (7% sugar+ 0.07% citric acid in spring water and 0.0267% encapsulated proflavor) and compared against a control (contains everything except the proflavor). Various panelists rated the solution containing the encapsulated proflavor as "fresh", "juicy" and "fruity". The sample was preferred over the control.

The invention claimed is:

1. A glass particle or bead composition comprising:
   a) a compound selected from the group consisting of a compound of Formula I

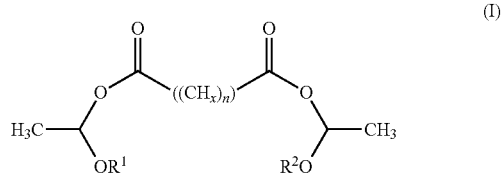

wherein $R^1$ and $R^2$ are independently selected from a branched or straight $C_1$-$C_4$ alkyl and a $C_1$-$C_4$ alkenyl, n is 1, 2, 3, 4, 5 or 6 and x is independently 0, 1 or 2 provided that when n is 1, x is 2, and 5-(2-(1-ethoxyethoxy)propan-2-yl)-2-methyl-2-vinyltetrahydrofuran; and
   b) a carrier comprising a carbohydrate wherein the carrier is provided in an amount, by weight, of up to about 90% of the total weight of the particle; and
   c) water.

2. The compound as recited in claim 1 wherein $R^1$ and $R^2$ are independently a straight or branched $C_1$-$C_4$ alkyl.

3. The compound as recited in claim 2 wherein $R^1$ and $R^2$ are independently selected from the group consisting of methyl, ethyl, propyl, and butyl.

4. The compound as recited in claim 1, wherein n is 1 and x is 2.

5. The compound as recited in claim 1, wherein n is 2 and x is independently 0, 1 or 2.

6. The compound as recited in claim 1, wherein n is 3, 4, 5 or 6 and x is independently 0, 1 or 2.

7. The composition as recited in claim 1, wherein the compound is selected from the group consisting of bis(1-ethoxyethyl) succinate; bis(1-ethoxyethyl) adipate; bis(1-ethoxyethyl) fumarate; bis(1-propoxyethyl) succinate; bis(1-propoxyethyl) adipate; bis(1-propoxyethyl) fumarate; bis(1-butoxyethyl) succinate; bis(1-butoxyethyl) adipate, and bis(1-butoxyethyl) fumarate.

8. The composition as recited in claim 1 wherein the compound is 5-(2-(1-ethoxyethoxy)propan-2-yl)-2-methyl-2-vinyltetrahydrofuran.

9. The composition as recited in claim 1, wherein the composition is a granule having a size greater than or equal to about 100 micrometers.

10. The composition as recited in claim 9 wherein the granule has a size in a range of about 100 μm up to about 5 mm (millimeters).

11. The composition as recited in claim 1, wherein the carrier comprises an emulsifier in an amount of from 0% up to about 100% by weight of the total weight of the carrier.

12. A method of releasing acetaldehyde into an aqueous solution comprising delivering a composition as defined in claim 1 to the aqueous solution.

13. A method to confer, enhance, improve or modify the flavor or aroma of a flavored article comprising adding to said flavor or flavored article an effective amount of at least one composition of claim 1.

14. A method of making a glass particle composition comprising:
   i) blending in an extruder a compound as defined in claim 1 with:
      a. a carrier comprised of a carbohydrate;
      b. a lubricant;
      c. water; and optionally
      d. an emulsifier;
   ii) heating the blend to a temperature sufficient to form a molten mass;
   iii) extruding the molten mass;
   iv) cutting the molten mass into granules; and
   v) allowing the granules to cool to form a glassy particle.

* * * * *

UNITED STATES PATENT AND TRADEMARK OFFICE
CERTIFICATE OF CORRECTION

PATENT NO. : 10,638,782 B2
APPLICATION NO. : 15/539013
DATED : May 5, 2020
INVENTOR(S) : Gary B. Womack Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 240 days.

Signed and Sealed this
Thirty-first Day of January, 2023

Katherine Kelly Vidal
*Director of the United States Patent and Trademark Office*